United States Patent

Inamoto et al.

[11] 3,985,803
[45] Oct. 12, 1976

[54] 2-HALOADAMANTYL-(1)-ACETAMIDES

[75] Inventors: Yoshiaki Inamoto; Hirokazu Nakayama; Naotake Takaishi, all of Wakayama, Japan

[73] Assignee: Kao Soap Co., Ltd., Tokyo, Japan

[22] Filed: June 26, 1974

[21] Appl. No.: 483,105

[30] Foreign Application Priority Data
June 29, 1973 Japan.............................. 48-73368

[52] U.S. Cl. ........................ 260/557 B; 204/158 R; 424/274
[51] Int. Cl.²........................................ C07C 103/19
[58] Field of Search...................... 260/557 B, 563 P

[56] References Cited
UNITED STATES PATENTS

| | | | |
|---|---|---|---|
| 3,218,355 | 11/1965 | Paulshock ...................... | 260/557 B |
| 3,591,642 | 7/1971 | Szinai et al. ................. | 260/563 P X |
| 3,644,356 | 2/1972 | Chakrabarti et al. ........ | 260/557 B X |
| 3,654,301 | 4/1972 | Chakrabarti................. | 260/563 P X |
| 3,789,072 | 1/1974 | Bernstein ........................ | 260/557 B |

OTHER PUBLICATIONS
Lunn et al., J. Chem. Soc. (C), 1968, pp. 1657–1660.
"Synthesis of Adamantane Derivatives," Sasaki et al., Bull. Chem. Soc. Japan, 1968, 41(1), pp. 238–240.
"Anodic Acetamidation of Adamantane and 1-Haloadamantanes," Koch et al., Tetrahedron Letters No. 9, pp. 693–696 (1973).

*Primary Examiner*—Robert V. Hines
*Assistant Examiner*—Thomas A. Waltz
*Attorney, Agent, or Firm*—Woodhams, Blanchard and Flynn

[57] ABSTRACT

A process for preparing 2-haloadamantyl-(1)-acetamides of the formula I

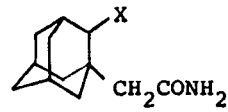

I wherein X is chloro, bromo or iodo, in which an N-haloadamantyl-(1)-acetamide of the formula II

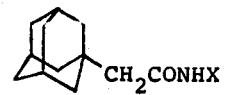

II wherein X is as defined above, is subjected to photochemical irradiation.

1 Claim, No Drawings

2-HALOADAMANTYL-(1)-ACETAMIDES

BACKGROUND OF THE INVENTION

FIELD OF THE INVENTION

This invention relates to novel compounds, 2-haloadamantyl-(1)-acetamides, and to a process for preparing those compounds.

2-Haloadamantyl-(1)-acetamides prepared according to the process of this invention are expected to have various biological activities. They are also valuable substances that can be used as starting materials for the synthesis of known, useful 1,2-disubstituted adamantanes.

SUMMARY OF THE INVENTION

We have discovered that when N-haloadamantyl-(1)-acetamide is irradiated with actinic radiation in the visible or ultraviolet light range of wave length, as is illustrated in the following reaction equation (1),

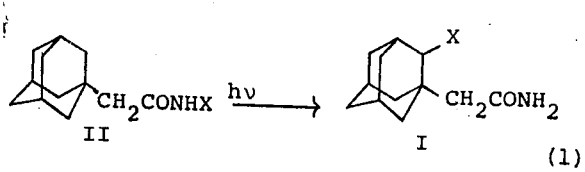

the halogen transfers from the nitrogen atom to the adjacent secondary carbon atom, whereby 2-haloadamantyl-(1)-acetamide is formed in good yield.

DESCRIPTION OF THE PRIOR ART

There are known adamantane derivatives having substituent(s) on the tertiary or bridgehead carbons, such as compounds represented by the following formulae III and IV

wherein Y and Z represent various substituents. These can be synthesized by a one-step process from adamantane, and various examples of such reactions can be cited [see, for example, R. C. Fort, Jr. and P. V. R. Schleyer, Chem. Revs., 64, 277 (1963); and Y. Inamoto and H. Nakayama, Synthetic Commun., 1, 133 (1964)].

However, as regards processes for synthesizing in good yield by a one step reaction, adamantane substances having a substituent on a secondary carbon atom, such as shown by the following formula V

there is known only one example, namely, the synthesis of 2-adamantone represented by the following reaction equation (2) [see H. W. Geluk and J. L. M. A. Schlatmann, Tetrahedron Letters, 24, 5361, 5369 (1968) and Rec. Trav. Chim., 90, 516 (1971)]:

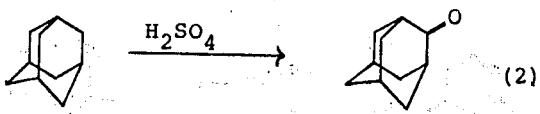

The difference between the ease of the formation of adamantyl-(1) and adamantyl-(2) derivatives is based on the difference in the ease of formation and stability between the adamantyl-(1) cation and the adamantyl-(2) cation or between the adamantyl-(1) radical and the adamantyl-(2) radical. Accordingly, 2-substituted adamantanes as represented by the above formula V are generally synthesized from 2-adamantanone as shown by the following reaction equation (3) [see, for example, R. C. Fort, Jr. and P. V. R. Schleyer, Chem. Revs., 64, 277 (1964)]:

wherein Y represents a substituent.

Accordingly, the well-known processes for the synthesis of 2-substituted adamantanes usually require more steps than those for the synthesis of 1-substituted adamantanes. Many more steps are required for the synthesis of 1,2-disubstituted adamantanes. For these reasons examples of the synthesis of 1,2-disubstituted adamantanes are very few. The known instances in which 1,2-disubstituted adamantanes have been synthesized by a one step reaction are those shown by the following reaction equatons (4) to (9):

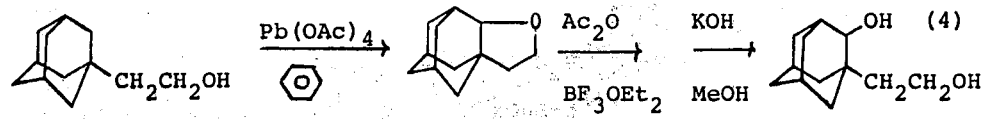

(M.A. McKervey Chem. Ind., 1967, 1971)

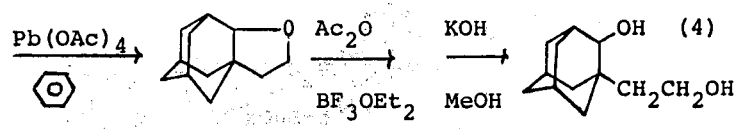

-continued

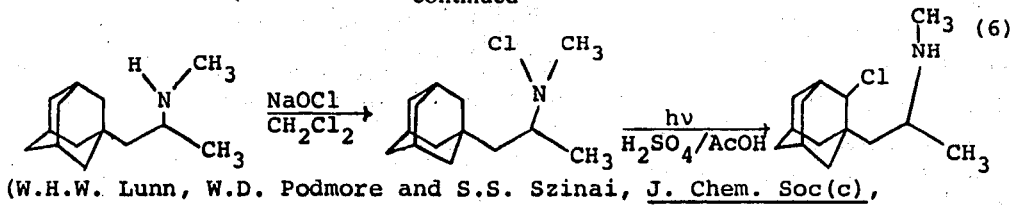

(W.H.W. Lunn, W.D. Podmore and S.S. Szinai, *J. Chem. Soc(c)*, 1968, 1657)

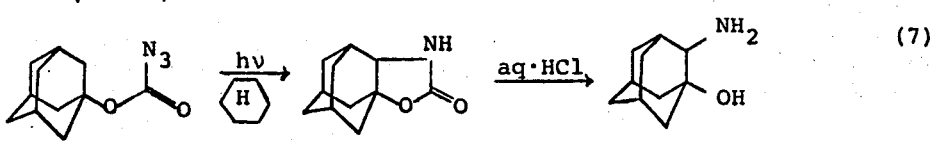

(W.V. Curran and R.B. Angier, *Chem. Commun.*, 1967, 563)

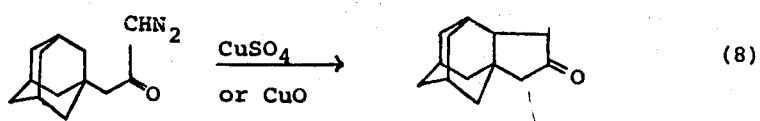

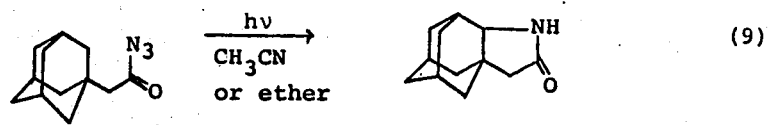

(J.K. Chakrabarti, S.S. Szinai and A. Todd, *J. Chem. Soc(C)*, 1970, 1303)

DETAILED DESCRIPTION OF THE INVENTION

According to the invention there is provided a process for preparing 2-haloadamantyl-(1)-acetamides of the formula I

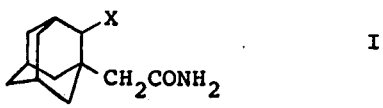

wherein X is chloro, bromo or iodo, in which an N-haloadamantyl-(1)-acetamide of the formula II wherein X is as defined above, is subjected to photochemical irradiation.

The process of this invention can easily be performed by subjecting the starting N-haloadamantyl-(1)-acetamide of the formula II to irradiation with visible or ultraviolet light, i.e. light having a wave length of from 50 to 7,500 angstroms.

The starting material N-haloadamantyl-(1)-acetamide of the formula II, as in the case of ordinary aliphatic N-haloamides, can be synthesized by reacting halogen with adamantyl-(1)-acetamide in the presence of base, for example, potassium hydroxide, as shown in the following reaction equation (10).

The product I of the present process can also be obtained directly from adamant-(1)-ylacetamide by the action of t-butyl hypohalite under the irradiation of light, whereby the intermediate N-haloadamant-(1)-ylacetamide is formed in situ which then rearranges to give the desired product I.

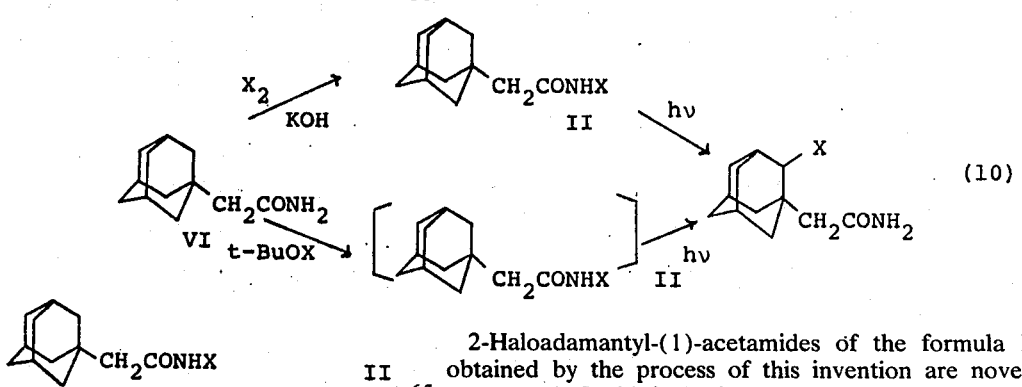

2-Haloadamantyl-(1)-acetamides of the formula I obtained by the process of this invention are novel compounds. In this invention, the structure of the product I was determined by elemental analysis and by various spectra, and it was also confirmed by treating the obtained compound I with sodium ethylate to convert it to a known compound, dihydroadamantano[2,1-b]-pyrrole-2(3H)-one of the formula VIII, as is shown by the following reaction equation (11) [H. Wamhoff and F. Korte, Chem. Ber., 100, 2122 (1967)]:

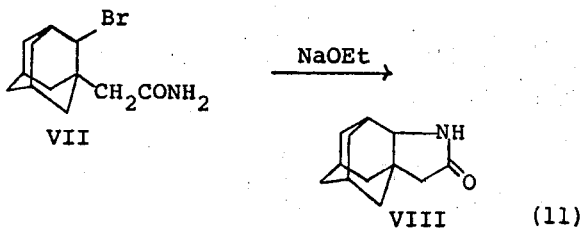

As an example of the use of the novel compound of formula I as an intermediate for preparing known useful compounds, the above-mentioned compound VII (an example of a compound of formula I) can be transformed to compound VIII, as described above. Compound VIII can be transformed by treating it with a reducing agent such as lithium aluminum hydride, under conventional conditions, to form a compound of the formula IX, namely, tetrahydroadamantano[2,1-b]pyrrole,

Compound IX is a known compound useful as a central nervous system depressant for warm blooded animals (U.S. Pat. No. 3,668,220).

To perform the process of this invention, because the starting material N-haloadamantyl-(1)-acetamides of the formula II are solid, it is advantageous to carry out the reaction in the presence of a solvent. Any inert solvent that can dissolve the starting N-haloadamantyl-(1)-acetamides of the formula II and are incapable of reacting with both the starting compounds and products can be used as a solvent in this invention. In view of the ease of isolating the product, it is preferred to use solvents having low boiling points. As solvents satisfying requirements, there can be mentioned, for example, halogenated lower hydrocarbons such as methylene chloride and dichloroethane (except that carbon tetrachloride and chloroform cannot be used as solvents because they react with adamanthane under irradiation of light to form chlorine-substituted adamantanes), ethers such as diethyl ether and di-isopropyl ether, lower aliphatic nitriles such as acetonitrile and propionitrile, benzene and the like. Radiation energy in the ultraviolet and visible light wave length range can be used for irradiation, but the use of shorter wave length radiation energy is preferred. In practice, the use of a mercury lamp or the like as a light source is most convenient and effective.

This invention will now be described in greater detail by reference to the following illustrative Examples. Processes for the synthesis of the starting material N-haloadamantyl-(1)-acetamides and for the identification of 2-haloadamantyl-(1)-acetamides are described in the following Preparations.

Preparation 1

Synthesis of N-bromo-adamantyl-(1)-acetamide II

A four-necked flask was charged with 29 g of adamantyl-(1)-acetamide, 24 g of bromine and 100 ml of chloroform, and 15 ml of 50 percent aqueous potassium hydroxide was added dropwise while the reaction mixture was kept at 0° to 5° C. by external cooling with an ice bath. After completion of the addition, the mixture was agitated at the same temperature for a further period of 3 hours. Then, 20 g of sodium chloride and 100 ml of chloroform were added to the reaction mixture, and the mixture was heated at 40° C. under vigorous stirring for several minutes and then cooled to room temperature. The chloroform layer was separated, and the water layer was extracted three times each time with 100 ml of chloroform. The chloroform extracts were combined, dried over anhydrous sodium sulfate and filtered. Then, 100 ml of n-hexane was added to the chloroform solution and the mixture was allowed to stand still for 1 hour. The resulting crystals were separated by filtration, washed with n-hexane and dried in a vacuum desiccator to give 10.4 g (yield: 25.4 wt.%) of N-bromoadamantyl-(1)-acetamide of the formula II having a melting point of 112° to 113° C. and a purity of 90.4 wt.% (as determined by iodometric tetration).

EXAMPLE 1

Preparation of 2-bromoadamantyl-(1)-acetamide I

A photochemical reaction tube composed of quartz was charged with 1 g of N-bromoadamantyl-(1)-acetamide prepared in Preparation 1 and 100 ml of methylene chloride as solvent, and the mixture was exposed for 2 hours to light emitted from a high pressure mercury lamp while being maintained at a temperature of 0° to 5° C. Aliquots were removed from time to time to test for the presence of the remaining N-bromoadamantyl-(1)-acetamide with the aid of a potassium iodide solution.

After all the starting N-bromoamide had reacted, removal of methylene chloride from the reaction mixture by distillation under reduced pressure gave 0.97 g of crystals as the residue. The residue was fractionated on a silica gel column using chloroform-acetone as the eluant to obtain 0.65 g of the desired product I. Recrystallization from methanol-n-hexane gave pure 2-bromoadamantyl-(1)-acetamide I, melting at 156° to 157.5° C.

Elemental Analysis:
Found: C, 52.2; H, 6.8; Br. 30.6; N, 4.8; O, 6.2%
Calculated for C$_{12}$H$_{18}$BrNO: C, 52.95; H, 6.67; Br, 29.36; N, 5.15; O, 5.88%.

ir Spectrum (KBr) (cm$^{-1}$):
3350(m), 3300(shoulder), 3180(m); νN-H(amide), 1670(s), 1640(shoulder; νC=O (amide), 1610(m); δNH nmr Spectrum (CDCl) (δ):
58.0(s, 2H, CHNH$_2$), 4.72(s,

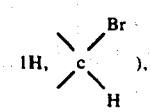

2.6-1.2(complicated m, 15H)
ms Spectrum (m/e (%)):
273(M12) (95); 271 (M) (100)

Preparation 2

Structure determination of 2-bromoadamantyl-(1)-acetamide

The structure of the rearrangement product obtained in Example 1 was determined as being 2-bromoadamantyl-(1)-acetamide I by the elemental analysis and ir, nmr and ms spectra. Further, from the fact that the known compound dihydroadamantano[2,1-b]-pyrrole-2(3H)-one VIII was obtained by the treatment of the product of Example 1 with sodium ethylate, it was confirmed that the product of Example 1 was 2-bromoadamantyl-(1)-acetamide I. The experimental procedure for this conversion is described below.

One and one-half ml of anhydrous ethanol containing 0.034 g of metallic sodium was mixed with 2 ml of anhydrous ethanol containing 0.4 g of the above rearrangement product, and the mixture was heated to reflux for about 2 hours. Sodium bromide thereby formed was removed by filtration, and ethanol was distilled off from the filtrate under reduced pressure to give 0.22 g of the product as the residue (yield: 78 wt.%). Recrystallization from chloroform-petroleum ether gave crystals of dihydroadamantano[2,1-b]pyrrole-2(3H)-one melting at 153° to 155° C.
Elemental Analysis:
Found: C, 75.5; H, 9.0; N, 7.32; O, 8.4%.
Calculated for $C_{12}H_{17}NO$: C, 75.35; H, 8.96; N, 7.32; O, 8.36%.
The compound showed no melting point depression on admixture with an authentic specimen prepared by the method of Chakrabarti, et al. (loc. cit.). Comparison of ir, nmr and ms spectra also confirmed the identity of the two samples.

Preparation 3

Preparation of N-bromoadamantyl-(1)-acetamide (II) using tert-butyl hypobromite

Nineteen and three tenths gram of adamantyl-(1)-acetamide VI was dissolved in 100 ml of methylene chloride, and 19 g of tert-butyl hypobromite (purity: 79.4 %) was added to the solution. The resulting mixture was stirred at room temperature for 1 hour in the dark. After methylene chloride and low-boiling fractions were distilled off from the reaction mixture under reduced pressure at room temperature, crude crystalline N-bromoadamantyl-(1)-acetamide II was obtained as the residue. The crude crystals were washed with n-hexane and dried at room temperature under reduced pressure to give 26.5 g (yield: 97.4%) of the desired product having a melting point of 112° to 113° C. and a purity of 89.4% (as determined by iodometric titration).

EXAMPLE 2

In the same manner as described in Example 1, 1 g of N-bromoadamantyl-(1)-acetamide II prepared in Preparation 3 was subjected to irradiation. Processing the reaction mixture in the same way as described in Example 1 gave 0.5 g (yield: 50 wt.%) of 2-bromoadamantyl-(1)-acetamide I melting at 156° to 157.5° C.
Elemental Analysis:
Found: C, 52.4; H, 6.6; Br, 29.0; N, 5.1; O, 6.2%.
Calculated for $C_{12}H_{18}BrNO$: C, 52.95; H, 6.67; Br, 29.36; N, 5.15; O, 5.88%.

The ir, nmr and ms spectra of the product were in complete agreement with those of the product obtained in Example 1.

EXAMPLE 3

This Example illustrates a one-step procedure for obtaining the desired 2-bromoadamant-(1)-ylacetamide from adamantyl-(1)-acetamide.

One gram of adamantyl-(1)-acetamide was dissolved in 10 g of methylene chloride, and 1 g of tert-butyl hypobromite (purity: 79.4 wt.%) was added to the solution. The resulting solution was stirred at room temperature for 1 hour in the dark. The reaction mixture was then diluted with 90 ml. of methylene chloride, and the solution was irradiated in the same manner as described in Example 1. Processing the reaction mixture as described in Example 1 gave 0.9 g (yield: 63 wt.%) of 2-bromoadamantyl-(1)-acetamide I melting at 156° to 157.5° C.
Elemental Analysis:
Found: C, 52.5; H, 6.7; Br, 29.8; N, 4.8; O, 6.0%.
Calculated for $C_{12}H_{18}BrNO$: C, 52.95; H, 6.67; Br, 29.36; N, 5.15; O, 5.88%.
The ir, nmr and ms spectra of the product were completely in agreement with those of the product obtained in Example 1.

An example of converting compound VIII to compound IX is described in the following Preparation 4.

Preparation 4

Preparation of tetrahydroadamantano[2,1-b]pyrrole

A solution of 1.91 g (10 mmole) of dihydroadamantano[2,1-b]-pyrrole-2(3H)-one (VIII) in 10 ml of tetrahydrofuran was added dropwise under stirring to a slurry consisting of 0.46 g (12 mmole) of lithium aluminum hydride and 20 ml of tetrahydrofuran. The mixture was refluxed for 8 hours. Any residual lithium aluminum hydride was decomposed by adding 5 ml of ethyl acetate. Most of tetrahydrofuran was distilled off under a slightly diminished pressure, and 50 ml of ether was added to the residue. To the mixture was added dropwise 10 ml of water and then 20 ml of 20% sulfuric acid. The ether layer was separated, the aqueous layer being extracted twice with each 20 ml of ether. The aqueous layer was then made strongly alkaline by adding 25% sodium hydroxide solution, and then extracted three times with each 20 ml of ether. The etherial solution was dried over anydrous potassium carbonate, and the ether was distilled off. The residue was distilled under a diminished pressure to give tetrahydroadamantano[2,1-b]pyrrolidine (IX).

The embodiments of this invention in which an exclusive property or privilege is claimed are defined as follows:

1. A compound of the formula

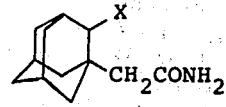

wherein X is chloro, bromo or iodo.

* * * * *